United States Patent [19]
Giannobile et al.

[11] Patent Number: 5,516,699
[45] Date of Patent: May 14, 1996

[54] PYRIDINOLINE CROSSLINKS AS MARKERS OF PERIODONTAL AND PERI-IMPLANT DISEASE ACTIVITY

[75] Inventors: William V. Giannobile, Waltham; Ray C. Williams, Belmont; Samuel E. Lynch, Grafton, all of Mass.

[73] Assignees: Institute of Molecular Biology, Inc., Worcester; President and Fellows of Harvard College, Cambridge, both of Mass.

[21] Appl. No.: 197,131

[22] Filed: Feb. 16, 1994

[51] Int. Cl.$^6$ .................................................. G01N 33/00
[52] U.S. Cl. ................... 436/96; 436/97; 436/98; 436/811
[58] Field of Search ................... 436/63, 96–98, 436/811

[56] References Cited

PUBLICATIONS

Gertz et al., J. Bone Miner. Res. 9:135–142 (1994).
Giannobile et al., J. Periodont. 64:186–190 (1993).
Risteli et al., Clin. Chem 39:635–640 (1993).
Seyedin et al., J. Bone Miner. Res. 8:635–641 (1993).
Eriksen et al., J. Bone Miner. Res. 8:127–132 (1993).
Elomaa et al., Br. J. Cancer 66:337–341 (1992).
Kunimatsu et al., J. Periodont. Res. 25:69–73 (1990).
Cox and Eley, J. Periodont. Res. 24:353–361 (1989).
Beighton and Life, Archs. Oral Biol. 34:8430846 (1989).
Cox and Eley, J. Periodont. Res. 24:41–44 (1989).
Jeffcoat et al., Adv. Dent. Res. 1:80–84 (1987).
Binder et al., J. Periodont. Res. 22:14–19 (1987).
Bowers et al., J. Periodontol 60:448–451 (1987).
Kryshtalskyj et al., J. Periodont. Res. 22:264–269 (1987).
Lamster et al., J. Periodont. 56:139–147 (1985).
Black D. et al.; "Quantitiative Analysis of the Pryridinium Crosslinks of Collagen in Urine Using Ion–paired Reversed–Phase High Performance Liquid Chromatography"; Anal. Biochem. 169:197–203 (1989).
Fujimoto D. et al.; "Analysis of Pyridinoline, A Cross–Linking Compound of Collagen Fibers, in Human Urine"; J. Biochem. 94:1133–1136 (1983).
Gunja–Smith Z. et al.; "Collagen Cross–Lining Compounds in Human Urine"; Biochem J. 197:759–762 (1981).
Haffajee A. D. et al.; "Clinical Risk Indicators for Periodontal Attachment Loss"; J. Clin. Periodontol 18:117–125 (1991).
Hanson D. A. et al.; "A Specific Immunoassay for Monitoring Human Bone Resorption:Quantitation of Type I Collagen Cross–Linked N–Telopeptides in Urine"; J. Bone and Mineral Research 7:1251–1258 (1992).
Hassager C. et al.; "Diurnal Variation in Serum Markers of Type I Collagen Synthesis and Degradation in Healthy Premenopausal Women"; J. Bone and Mineral Research 7:1307–1311 (1992).
Robins S. P. et al.; "Measurement of the Cross–Linking Compound, Pyridinoline, in Urine as an Index of Collaen Degradation in Joint Disease"Ann Rheum Dis. 46:969–973 (1986).
Rosen H. N. et al.; "Specificity of Urinary Excretion of Cross–Linked N–Telopeptides of Type I Collagen as a Marker of Bone Turnover"; Calcif. Tissue Int. 54:26–29 (1994).
Seibel M. J. et al.; "Urinary Hydroxy–pryidinium Cross Links Provide Indices of Cartliage and Bone Involvement in Arthritic Diseases"; J. Rheumatol 16:7:964–970 (1989).

(List continued on next page.)

Primary Examiner—David A. Redding
Attorney, Agent, or Firm—Fish & Richardson

[57] ABSTRACT

A method of diagnosing severity of periodontal disease or peri-implant disease in a human patient, involving a) obtaining a sample of tissue or gingival crevicular or other fluid from the mouth of said patient, or a blood or urine sample from the patient, and b) measuring a pyridinoline crosslinked compound in the sample as a measure of severity of disease.

11 Claims, 3 Drawing Sheets

*$P < 0.05$ as compared to Health

OTHER PUBLICATIONS

Uebelhart D. et al.; "Effect of Menopause and Hormone Replacement Therapy on the Urinary Excretion of Pyridinium Cross-Links"; *J. Clin. Endocrinol. Metab.* 72:367–373 (1991).

Uebelhart D. et al.; "Urinary Excretion of Pyridinium Crosslinks: A New Marker of Bone Resorption in Metabolic Bone Disease"; *Bone and Mineral* 8:87–96 (1990).

Robins, Biochem. J. 207:617–620 (1982).

Ishikawa and Cimasoni, Archs Oral Biol. 15:1401–1404 (1970).

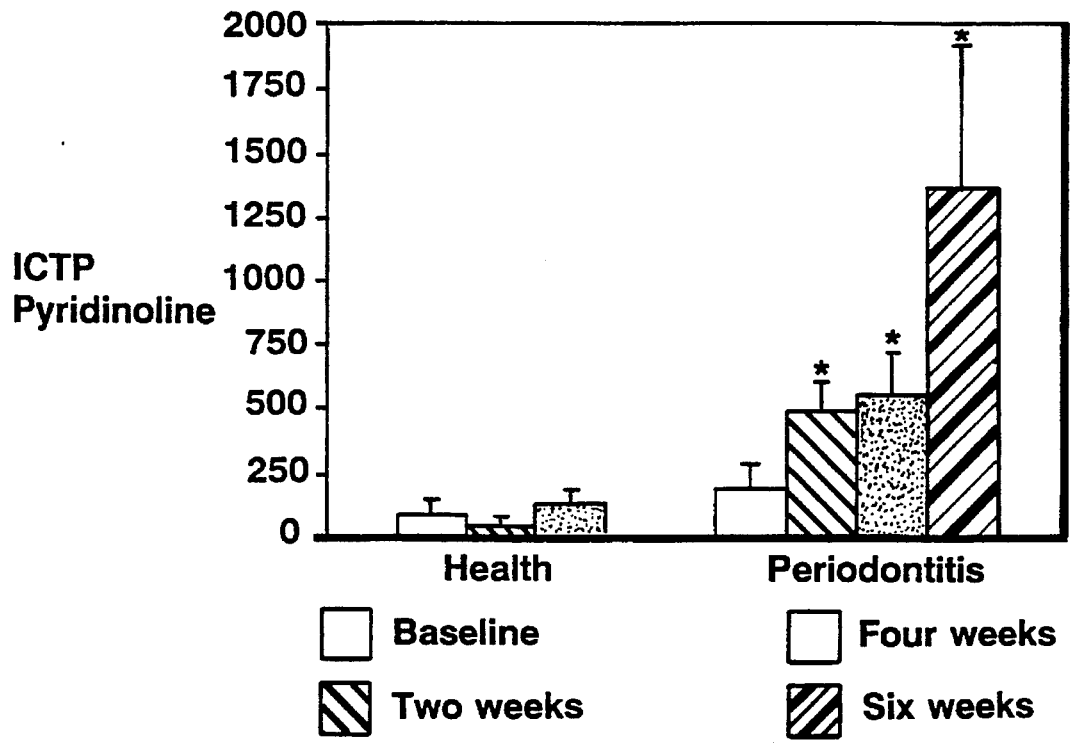
FIG. 2  *P<0.05 as compared to Health
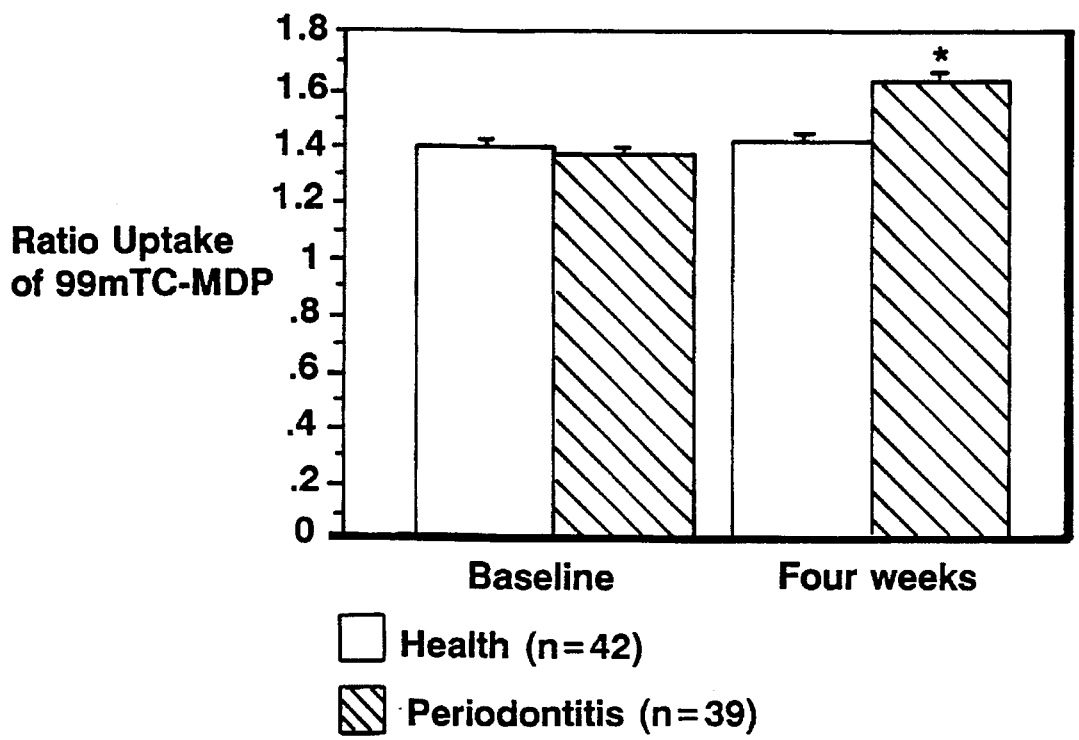
FIG. 3  *P<0.05 compared to Health

PYRIDINOLINE CROSSLINKS AS MARKERS OF PERIODONTAL AND PERI-IMPLANT DISEASE ACTIVITY

BACKGROUND OF THE INVENTION

This invention relates to measuring severity of periodontal and peri-implant disease.

Periodontal and peri-implant disease activity presently are diagnosed by clinical parameters such as pocket depth, bleeding on probing, and radiographs. These parameters have limitations in that they lack ability to predict future attachment loss, and provide information only on the existence of past disease activity. The need for diagnostics in periodontology which are predictive markers of active periodontitis is a focus of present research.

Periodontal disease is a general term used to describe specific diseases that affect the gingiva, as well as the supporting connective tissues and alveolar bone which anchor the teeth in the jaws. The periodontal diseases are among the most common infectious diseases in humans. In the last fifteen years, with the decline of dental caries in children aged 6–18, and better prevention programs for the general population, periodontal disease leading to tooth loss has assumed even greater importance. As more teeth are retained due to reduced caries, more teeth are at risk to be affected by periodontal disease (Shaw, J. H., N. Eng. J. Med. (1987) 317:996; Williams, R. C., N. Eng. J. Med. (1990) 332:373). Thus, the recognition and diagnosis of periodontal disease has become even more important.

The use of clinical parameters for the diagnosis of periodontal disease has numerous limitations. For example, Haffajee and co-workers (Haffajee, A. D., et al., J. Periodontal (1991) 18:117) have demonstrated that no clinical parameters have been shown to be predictive for periodontal disease activity. Thus there have been intensive research efforts to develop diagnostic tests for periodontal disease evaluation. Over 40 different tests for gingival crevicular fluid (GCF) components have been studied, e.g., collagenase (Villela, B. et al., J. Periodont. Res. (1987) 22:264), alkaline phosphatase (Ishikawa, I. et al., Arch. Oral. Biol., (1970) 15:1401; Binder, T. A. et al., J. Periodont. Res. (1987) 22:14), cathepsin-like activities (Kunimatsu, K. et al., J. Periodont. Res. (1990) 25:69; Cox, S. W. et al., J. Periodont. Res. (1989) 24:353; Cox, S. W. et al., J. Periodont. Res. (1989) 24:41; Beighton, D. and Life, J. S. C., Arch Oral. Biol. (1989) 34:843), and β-glucuronidase (Lamster I. B. et al., J. Periodontol. (1985) 56:139).

Despite the plethora of such components, there are at present no diagnostic tests available which have been demonstrated to be highly predictive for future bone and attachment loss in periodontal disease. As the breakdown of these components is the ultimate concern of the practitioner, their destruction should be evaluated. Connective tissue-associated proteins such as glycosaminoglycans (Giannobile, W. V. et al., J. Periodontol. (1993) 64:186) and osteonectin (Bowers, M. R. et al., J. Periodontol (1989) 60:448) have been found in GCF from patients exhibiting clinical signs of periodontitis. However, no longitudinal studies have been performed which relate these components to future bone or attachment loss.

Collagen makes up approximately 90% of the organic matrix of bone. Collagen type I is the most abundant collagen of osseous tissues (Deftos, L. J., Clin. Chem. (1991) 3/7:1143). Following procollagen biosynthesis and its release into the maturing extracellular matrix, collagen molecules form crosslinks which provide additional mechanical stability to the matrix (Miyahara, M. et al., J. Biol. Chem. (19082) 257:8442). These intermolecular crosslinks are formed between the terminal, nonhelical telopeptide regions on one collagen molecule and the helical parts or another chain. The resultant crosslinks are initially bivalent, which in turn become multivalent complexes with collagen matrix maturation (Last, J. A. et al., Int. J. Biochem. (1990) 22:559). Crosslink biosynthesis is initiated by lysine and hydroxylysine residues. There are two major types of crosslinks: (1) Enzyme lysyl oxidase initiated crosslinks, and (2) derivatives from nonenzymatically glycosylated lysine and hydroxylysine residues. Pyridinoline crosslinked carboxy terminal telopeptide of type I collagen (ICTP) are derived from the carboxyterminal telopeptide regions of type I collagen which has been cross-linked via pyridinoline. ICTP is liberated during the degradation of type I collagen. ICTP is found in an immunochemically intact form in blood, where it appears to be derived from bone resorption. ICTP crosslinked compound contains three peptides, the principal one of which is the carboxyterminal telopeptide of the $\alpha 1(I)$ chain, which is considerably smaller than the ICTP peptide determined from SDS-PAGE (Risteli, J. et al., Clin. Chem. (1993), 39:635).

Collagen also serves as precursor for another class of pyridinoline crosslinked compound: cross-linked N-telopeptides of type I collagen (NTP) (found on the N-terminal end of the original collagen type I molecule), hydroxylysylpyridinoline, (pyridinoline or HP) and lysylpyridinoline (deoxypyridinoline or LP) which are measurable in urine (Seyedin S. M. et al., J. Bone Miner. Res. (1993), 8:635; Gertz, B. J. et al., J. Bone Miner. Res. (1994), 9:135; Eriksen, E. F. et al. (1993), J. Bone Miner. Res., 8:127). These molecules, produced from the degradation of type I collagen (ICTP, NTP, HP and LP), are termed "Pyridinoline Crosslinks".

Changes in serum concentrations of ICTP crosslinked compound have been observed in some metabolic bone diseases where it correlates with the bone resorption rate measured either histomorphometrically or by calcium kinetic studies (Eriksen, E. F. et al., J. Bone Miner. Res. (1993), 8:127; Hassager, C. et al., Bone Miner. Res., (1992), 7:1307). Serum ICTP crosslinked compound also correlate with the urinary excretion of ICTP crosslinked compound, as measured by HPLC (Robins, S. P., Biochem. J. (19082), 207:617).

Increased serum concentrations of ICTP crosslinked compound are seen in conditions associated with increased lysis of bone, such as multiple myeloma, osteolytic metastases, rheumatoid arthritis, and immobilization (Elomaa, I. et al., Br. J. Cancer, (1992), 66:337). In addition, studies have shown that in postmenopausal women, estrogen treatment decreases serum ICTP crosslink concentrations.

SUMMARY OF THE INVENTION

The invention features a method of determining the progression of periodontal disease or peri-implant disease in a human patient, involving obtaining a sample of tissue, fluid, or gingival crevicular fluid from the mouth or a sample of blood or urine of the patient, and measuring pyridinoline crosslinked compound as a measure of disease progression.

In preferred embodiments, a level of greater than 50 ng/ml of ICTP in gingival crevicular fluid ("GCF") or more preferably 100 ng/ml or 50 pg/sample site is indicative of disease. Further, in preferred embodiments, a level of 6 ng/ml or greater in the peripheral blood or more preferably 10 ng/ml of ICTP is indicative of disease. Also included in the preferred embodiments, a level of 100 pmol/µmol creatinine of NTP in urine is indicative of disease; and a level of 150 nmol/µmol creatinine of HP or LP is indicative of disease. In addition, a level of 100 pmol of NTP in GCF or blood is indicative of disease; and a level of 150 µmol of HP or LP is indicative of disease.

The invention provides a quantitative measure of periodontal disease, and in addition can detect incipient and early stage disease, and not just advanced disease as current clinical techniques do. In addition, the method of the invention allows not just the detection and quantification of disease, but also permits precise localization of disease, so that treatment can be targeted to the tissues most severely affected.

Other features and advantages of the invention will be apparent from the following detailed description thereof, and from the claims.

DETAILED DESCRIPTION

The drawings are first briefly described.

Drawings FIG. 1 is a graph demonstrating the correlation between periodontitis and ICTP crosslinked compound in crevicular fluid.

FIG. 2 is a graph showing the difference in bone metabolic activity by 99mTc-MDP uptake in healthy vs. periodontitis sites in dogs.

FIG. 3 is a graph demonstrating the correlation between periodontitis and circulating ICTP crosslinked compound.

GCF Collection

Figure 1:
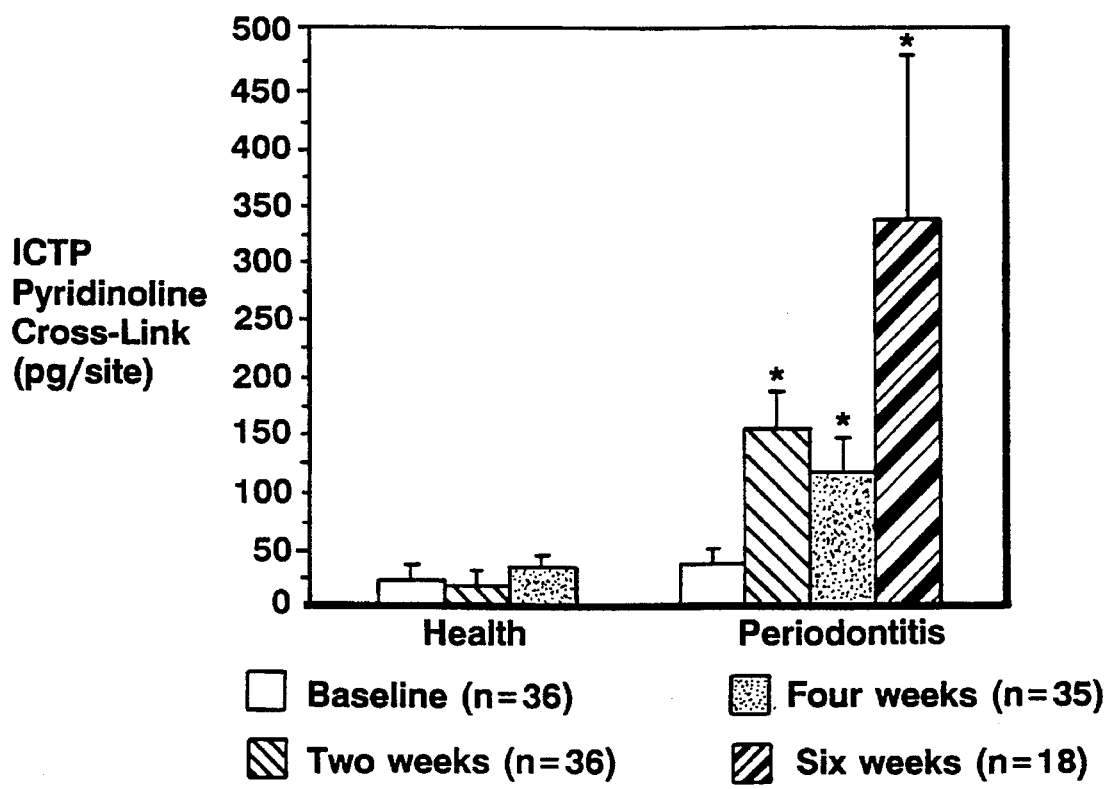

GCF is a secretion which is exuded from the sulcus between gum and tooth. When first formed, GCF does not mix with the saliva in the mouth, but only does so after it leaves the sulcus and enters the oral cavity. In collecting GCF for analysis according to the invention, it is desirable to minimize dilution of GCF with saliva. Thus the saliva in the vicinity of the sulcus from which GCF is to be collected is removed, preferably using cotton rolls in combination with compressed air, which is blown over the region.

Following air-drying, GCF is collected by placement of a strip of porous material such as methylcellulose filter paper into the sulcus and maintaining that material in the sulcus for about 30 seconds. The strip is inserted into the sulcus until slight resistance is detected. Following GCF collection, fluid volume is measured using a Peritron 6000 ™ measuring instrument or other similar device. The collected fluid is eluted from the filter strip using phosphate buffered saline containing proteinase inhibitors. Samples are stored frozen until needed for analysis. Prior to analysis, samples are allowed to thaw at room temperature and they are then assayed for ICTP crosslinked compound by any conventional technique, such as radioimmunoassay (RIA) or some other standard detection method, e.g., ELISA.

Canine Experiments

Dogs (two one-year old male beagles) are used to assess the measurement of ICTP crosslinked compound as a marker of periodontal disease activity. The left quadrants randomly serve as the experimental sites, while the right quadrants serve as control sites. Both animals receive an oral prophylaxis 14 days prior to initiation of the studies. The dogs are exposed to the following procedures.

Experimental periodontitis is induced in the left quadrants in both dogs in the following way: 3-0 silk ligatures are tied around the first through fourth maxillary and mandibular premolars in all four quadrants. The dogs are placed on a plaque-promoting diet of water-moistened Purina dog chow. The ligature induced periodontitis demonstrates heavy bacterial accumulation and leads to an immediate inflammatory response with subsequent resorption of bone. The control quadrants on the right do not have silk ligatures, but instead, oral hygiene procedures are routinely performed. The purpose of the monthly oral hygiene procedures is to maintain health of the gingiva in the control quadrants. There are 6 teeth/half mouth×2 sides/dog×1 radiographic sites/tooth=a total of 12 control sites and 12 experimental sites.

This condition of health and disease is verified by the use of subtraction radiography and nuclear medicine, which are utilized to quickly and accurately quantify bone resorption and to correlate these parameters with GCF levels of ICTP crosslinked compound between experimental and control sites.

Subtraction radiographic measurements are taken at the beginning of the ligature induced periodontitis period, denoted as baseline, and again at 2 weeks, 4 weeks, 6 weeks, 8 weeks, 10 weeks, 12 weeks, 16 weeks, and 6-months after onset of periodontitis, in both the experimental and control sites.

At baseline, 1-month, 2-months, 4-months and 6-months, both the experimental and control sites also have ICTP crosslinked compound sample measurements taken. There are 6 teeth/half-mouth×2 sides/dog 3 sample sites/tooth=a total of 18 control sites and 18 experimental sites.

In summary, the totals for sample analysis are as follows:

| Time point | Control Quadrants Number of ICTP Crosslink Samples | Number of Radiographic Sites | Experimental Quadrants Number of ICTP Crosslink Samples | Number of Radiographic Sites |
|---|---|---|---|---|
| BASELINE | 18 | 12 | 18 | 12 |
| 2 Weeks | 18 | 12 | 18 | 12 |
| 4 Weeks | 18 | 12 | 18 | 12 |
| 6 Weeks | 18 | 12 | 18 | 12 |
| 8 Weeks | 18 | 12 | 18 | 12 |
| 10 Weeks | 18 | 12 | 18 | 12 |
| 12 Weeks | 18 | 12 | 18 | 12 |
| 16 Weeks | 18 | 12 | 18 | 12 |
| 24 Weeks | 18 | 12 | 18 | 12 |
| TOTALS | 162 | 108 | 162 | 108 |

Gingival Crevicular Fluid (GCF) Collection

GCF is collected from the mesial, buccal and distal locations of the first premolar through fourth premolar in each quadrant from both dogs. The GCF is collected as described above with methylcellulose strips, and the volume determined with a Periotron 6000™. Samples are placed in 1 mL Eppendorf vials in a solution containing 55 µl of proteinase inhibitors (15 nM aprotenin and 1 mM phenylmethylsulfonylfluoride (PMSF)) in phosphate buffered saline (PBS), pH 7.4. The fluid is subsequently stored on ice, followed by elution from the collection device for a period of 60 minutes at 25° C. The samples are then stored at −20° to −80° C. until needed for ICTP crosslink analysis.

ICTP Crosslink Analysis

Frozen samples are allowed to thaw at room temperature for subsequent analysis of ICTP crosslinked compound by RIA (Risteli, J. et al., Clin. Chem. (1993), 39:635–640). All samples and reagents are allowed to come to room temperature. The samples and standards are set up in duplicate in 12×75 mm test tubes. Samples are aliquoted into tubes and 200 µL of rabbit anti-ICTP is added to each sample. 200 µL of [$^{125}$I]ICTP is added to all samples followed by mixing and incubation for 2 hours at 37° C. 500 µL of goat anti-rabbit IgG in a suspension with PEG is added to all tubes. The samples are vortexed and incubated for 30 minutes at 20°–25° C. The samples are followed by centrifugation for 30 minutes at 2,000×g at 4° C. The supernatant is immediately decanted from all samples. Using a gamma scintillation counter, standards of ICTP (1–50 ng/mL) are assessed along with GCF samples (ng/mL) will be plotted comparing B/Bo (%) versus ICTP concentration. The assay can detect as little as 0.34 ng/mL of ICTP. Serum and saliva samples from both dogs are evaluated for ICTP crosslink carboxy-terminal telopeptide of type I collagen content for comparison purposes.

Analysis of the Concentration of Peripheral Blood

Mid-morning peripheral blood samples are collected for analysis of ICTP pyridinoline crosslinked compounds at two-week intervals from baseline through 6 months post ligature-periodontitis induction (methods of ICTP analysis described above). Comparisons are made throughout the study with nuclear medicine and subtraction radiographic parameters of bone resorption (see FIGS. 2 and 3).

Analysis of The Concentration of Urinary Pyridinoline Cross-Links

For the measurement of urinary pyridinoline crosslinked compounds (i.e., NTP, HP and LP), 24 hour urine samples are assayed as described previously (Seyedin, S. M. et al., (1993), J. Bone Miner. Res., 8:635; Hanson, D. A. (1992), J. Bone Miner. Res., 7:1251). Samples are collected during estimated time points of active periodontal bony destruction in the dogs (at 3 months post-ligature induction) and following the initiation of oral hygiene procedures and return to health. Comparisons are made to illustrate differences in urinary pyridinoline cross-link levels between health and active disease. Significant differences are correlated with both nuclear medicine and subtraction radiographic indices of bone resorption.

Subtraction Radiographic Techniques

Standard radiographs taken at Baseline and 2, 4, 6, 8, 10, 12, 16, and 24 weeks are used to measure the loss of alveolar bone over time. Radiographs are exposed at 90 KVP, 15 Ma and 0.5 s and developed in an automatic film processor. The radiographs are then analyzed with a computer assisted method as follows: The radiographs were converted into subtraction images using a closed-circuit video system (GE model 4TES) camera coupled to an analog digital converter capable of storing an entire video frame in solid-state memory in one time frame (⅟₃₀ s). This device, a digital frame grabber (Imaging Technologies, PC Vision Frame Grabber) is capable of digitizing and storing image frames and has an information capacity of more than two million bits (512×512 pixels by 8 bits deep) utilizing an IBM PC AT™ as the central processing unit.

The images are placed in spatial register with the aid of a micromanipulator capable of orthogonal movement in two dimensions plus rotation in the same plane (Klinger). The first radiograph is stored in the computer's fixed disk drive using the full 256 (8 bits) gray levels of resolution. Registration of the second film to be compared is facilitated by continuously "grabbing" the image of the second radiograph while simultaneously displaying the subtraction between the first and second radiograph on the same video screen. Since slight variations in film processing or voltage to the X-ray tube may result in differences in contrast in the resultant films, the nonparametric gamma correction algorithm of Ruttiman (Ruttiman, U. E. et al., J. Periodont. Res. (1986) 21:486) is used to correct differences in contrast between the two films. Registration is achieved when the video screen is a uniform gray and the anatomical structures such as teeth are not clearly discernible.

To measure the loss of bone between the two radiographs, the distance between the CEJ and the height of the alveolar crest is determined for the mesial and distal root surfaces. The alveolar bone height is taken either at the alveolar crest (for longitudinal bone loss) or at the point where the PDL space becomes indistinct (at the base of the apparent infrabony defects). This measurement is converted for the magnification of the radiograph in the image processing system. Millimeters of bone loss at each site are determined from each radiograph. The radiographic images at 2 weeks are subtracted from the radiographs taken at baseline. Radiographs at 4 weeks are subtracted from the radiographs taken at baseline and so forth through 6 months. This provides multiple separate rates between each radiographic time interval (0, 0.5, 1, 1.5, 2, 2.5, 3, 4, and 6 months). Previous studies have shown that the error of this method in estimating bone loss is less than 0.08 mm on the original radiograph.

Nuclear Medicine Techniques

Nuclear medicine techniques have been used to detect changes in bony metabolism (Jeffcoat, M. K. et al., Adv. Dent. Res. (1987), 1:80). Since changes in metabolism precede changes in architecture, nuclear medicine techniques can be used to detect osseous abnormalities before the changes can be seen on radiographs, and to predict bone loss or its inhibition which will subsequently be seen radiographically. In an animal model, nuclear medicine techniques are used to extend and amplify the radiographic measurements of the ligature induced periodontitis on bone resorption by measuring bone metabolism. The technique used is as follows: At the beginning of the study (Baseline), both dogs are injected with 1.5 mCi/kg of $^{99}$Tc-MDP intravenously. Following a 60 minute period to allow for blood and soft tissue clearance of radiopharmaceutical, the alveolar bone uptake is measured.

A cadmium telluride semi-conductor probe detector is used to obtain measurement of uptake about the first through fourth premolars of each quadrant in both dogs. The uptake measurement for each site is divided by the uptake measured at the bony prominence dividing the dorsal and posterior skull surfaces. The use of ratios corrects the data for differences in injected dose and biological and physical decay of radiopharmaceutical, thereby facilitating comparison of uptake data between animals. At the end of 1-month, 2-months, 4-months and again at 6-months, the uptake of the radiopharmaceutical at each study site is repeated.

The efficacy of the method of the invention in determining the presence of disease based on ICTP crosslinked compound levels was demonstrated in an experiment, the results of which are graphically depicted in FIGS. 1–4, which display data generated from gingival crevicular fluid (GCF) and peripheral blood samples collected from dogs following induction of periodontitis from baseline through 6 weeks and corresponding radiopharmaceutical uptake (FIG. 3). Statistically significant increases ($P<0.05$) in GCF ICTP crosslinked compound levels/site (FIG. 1) and ng/ml (FIG. 2) were found in periodontitis sites from 2 through 6 weeks. GCF samples collected from healthy sites demonstrated only low levels of ICTP crosslinked compound at all time points.

Referring to FIG. 3, the increases in ICTP crosslink levels at 4 weeks correlated with significant elevations in radiopharmaceutical uptake of 99mTc-MDP in periodontitis sites, demonstrating correlation with heightened osseous metabolic activity (i.e., bone resorption).

Figure 4:
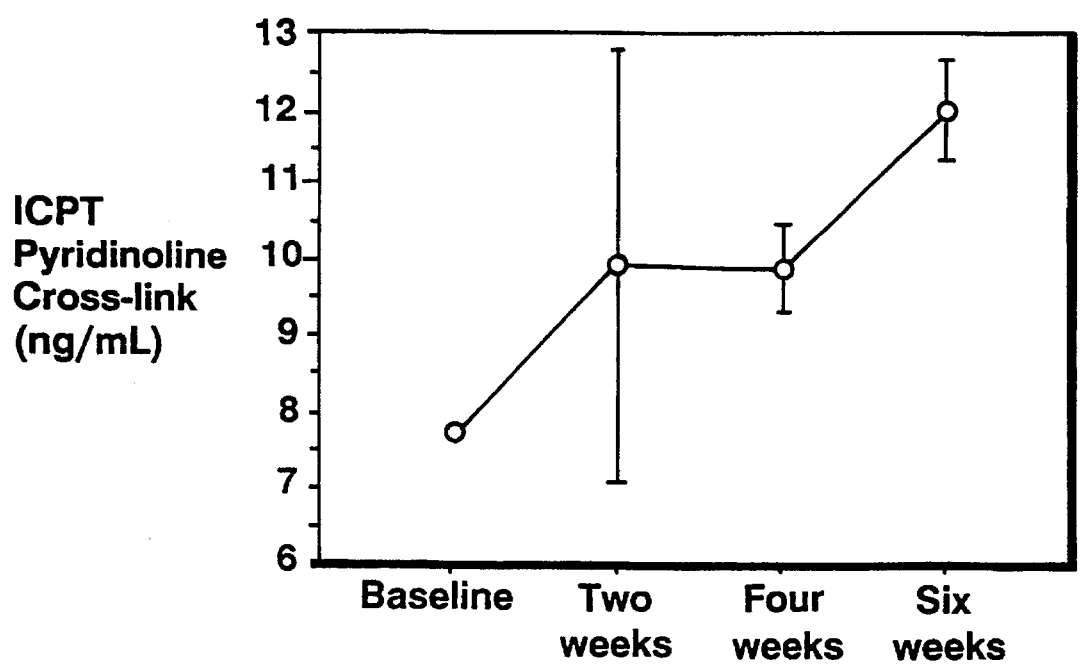
FIG. 4 is a graph demonstrating the correlation between circulating ICTP crosslink and periodontitis.

FIG. 4 demonstrates the effects of induction of periodontitis on circulating peripheral blood levels of ICTP pyridinoline crosslinked compound. Periodontitis was induced around the teeth on one side of the mouth while the contralateral sides were maintained in periodontal health. Note significant increases at 6 weeks as compared to baseline ($p<0.05$). This illustrates that periodontitis elevates systemic ICTP pyridinoline crosslinked compound levels as well as locally in the GCF (See FIG. 1).

Other embodiments are within the following claims.

What is claimed is:

1. A method of determining the presence or progression of periodontal disease or peri-implant disease in a mammal, said method comprising a) obtaining a sample of gingival crevicular fluid from the mouth of said mammal, and b) measuring a pyridinoline crosslinked compound in said sample as a measure of disease progression or risk.

2. The method set forth in claim 1, wherein an ICTP crosslinked compound level above 50 pg/sample site indicates the presence of periodontal or peri-implant disease.

3. The method as set forth as in claim 1, wherein said pyridinoline crosslinked compound is ICTP crosslinked compound, and an ICTP crosslinked compound level above 100 ng/ml in said fluid indicates the presence of a periodontal or peri-implant disease state.

4. The method set forth in claim 3, wherein an ICTP crosslinked compound level above 200 ng/ml in the sample indicates the presence for periodontal or peri-implant disease.

5. A method of determining the presence or progression of periodontal or peri-implant disease in a mammal, said method comprising a) obtaining a sample of blood from the mammal, and b) measuring a pyridinoline crosslinked compound in said sample as a measure of disease progression or presence.

6. The method set forth in claim 5, wherein said pyridinoline crosslinked compound is ICTP crosslinked compound, and an ICTP crosslinked compound level above 6 ng/ml in said sample indicates the presence for periodontal or peri-implant disease.

7. The method set forth in claim 6 wherein an ICTP crosslinked compound level above 10 ng/ml in said sample indicates the presence for periodontal or peri-implant disease activity.

8. The method of claim 1, wherein said pyridinoline crosslinked compound is NTP crosslinked compound.

9. The method set forth in claim 8, wherein an NTP crosslinked compound level above 75 pmol/sample indicates presence for periodontal or peri-implant disease.

10. The method of claim 1, wherein said pyridinoline crosslinked compound is HP and/or LP crosslinked compound.

11. The method set forth in claim 10, where an HP or LP crosslinked compound level above 60 nmol in said sample indicates presence for periodontal or peri-implant disease.

* * * * *

UNITED STATES PATENT AND TRADEMARK OFFICE
CERTIFICATE OF CORRECTION

PATENT NO. : 5,516,699

DATED : May 14, 1996

INVENTOR(S) : William V. Giannobile, Ray C. Williams, and Samuel E. Lynch

It is certified that error appears in the above-identified patent and that said Letters Patent is hereby corrected as shown below:

On the title page, item [56] and column 1 the title should read as follows: "PYRIDINOLINE CROSSLINKED COMPOUNDS AS MARKERS OF PERIODONTAL AND PERI-IMPLANT DISEASE ACTIVITY";

On title page, item [56], under "PUBLICATIONS", column 2, "Robins S.P. et al...", replace "Collaen" with --Collagen--;

Column 1, lines 1-4, replace the title as follows: "PYRIDINOLINE CROSSLINKED COMPOUNDS AS MARKERS OF PERIODONTAL AND PERI-IMPLANT DISEASE ACTIVITY";

Column 2, line 3, replace "(19082)" with --(1982)--;

Column 2, line 43, replace "compound" with --compounds--;

Column 2, line 45, replace "(19082)" with --(1982)--;

Column 2, line 63, replace "compound" with --compounds--;

Column 3, line 35, replace "crosslink and periodontitis" with --crosslinked compound and periodontitis--;

Column 5, line 3, replace "crosslink analysis" with --crosslinked compound analysis--;

UNITED STATES PATENT AND TRADEMARK OFFICE
CERTIFICATE OF CORRECTION

PATENT NO. : 5,516,699
DATED : May 14, 1996
INVENTOR(S) : William V. Giannobile, Ray C. Williams, and Samuel E. Lynch It is certified that error appears in the above-indentified patent and that said Letters Patent is hereby corrected as shown below:

Column 5, line 62, replace "(GE model 4TES)" with --(GE model 4TE5)--.

Signed and Sealed this

Fifth Day of November, 1996

Attest:

BRUCE LEHMAN

Attesting Officer    Commissioner of Patents and Trademarks